United States Patent
Zigler

(10) Patent No.: US 6,529,769 B2
(45) Date of Patent: Mar. 4, 2003

(54) APPARATUS FOR PERFORMING HYPERSPECTRAL ENDOSCOPY

(75) Inventor: Arie Zigler, Washington, DC (US)

(73) Assignee: APTI, Inc., Washington, DC (US)

( * ) Notice: Subject to any disclaimer, the term of this patent is extended or adjusted under 35 U.S.C. 154(b) by 15 days.

(21) Appl. No.: 09/802,125

(22) Filed: Mar. 8, 2001

(65) Prior Publication Data

US 2002/0128559 A1 Sep. 12, 2002

(51) Int. Cl.[7] ................................................. A61B 6/00
(52) U.S. Cl. .................. 600/478; 600/160; 356/326
(58) Field of Search .................. 600/476, 477, 600/478, 128, 138, 167, 152, 317, 108, 139, 153, 182, 425, 160; 356/326, 305, 341, 328, 318; 606/2; 348/69, 71, 137, 138, 141; 382/191, 100, 155, 232

(56) References Cited

U.S. PATENT DOCUMENTS

| | | | | |
|---|---|---|---|---|
| 4,802,461 A | * | 2/1989 | Cho | 600/108 |
| 4,941,456 A | * | 7/1990 | Wood et al. | 600/152 |
| 4,980,763 A | * | 12/1990 | Lia | 348/137 |
| 5,421,337 A | | 6/1995 | Richards-Kortum et al. | 128/665 |
| 5,507,287 A | | 4/1996 | Palcic et al. | 128/633 |
| 5,590,660 A | | 1/1997 | MacAulay et al. | 128/664 |
| 5,769,792 A | | 6/1998 | Palcic et al. | 600/477 |
| 5,782,770 A | * | 7/1998 | Mooradian et al. | 600/476 |
| 6,038,344 A | * | 3/2000 | Palmadesso et al. | 382/191 |
| 6,167,156 A | * | 12/2000 | Antoniades et al. | 382/100 |
| 6,373,568 B1 | * | 4/2002 | Miller et al. | 356/326 |
| 6,380,958 B1 | * | 4/2002 | Guendel et al. | 600/425 |

* cited by examiner

Primary Examiner—Tu Ba Hoang
(74) Attorney, Agent, or Firm—Rossi & Associates

(57) ABSTRACT

A hyperspectral imaging endoscopy apparatus is provided that utilizes spectral technology to acquire, process and exploit gastroscopic data. The apparatus allows for real time anomaly detection and identification. The apparatus includes an endoscope, a spectrometer and a processing unit that perform hyperspectral analysis on spectral data generated from the spectrometer. The endoscope and associated coupling optics are preferably optimized for cylindrical symmetry, thus allowing continuous inspection of gastrointestinal or arterial walls.

7 Claims, 2 Drawing Sheets

APPARATUS FOR PERFORMING HYPERSPECTRAL ENDOSCOPY

FIELD OF THE INVENTION

The invention relates in general to an apparatus for examining tissue for abnormalities or anomalies through the use of endoscopic examinations. More specifically, the invention relates to an endoscopic apparatus that utilizes hyperspectral analysis to detect abnormality or anomaly conditions in tissue.

BACKGROUND OF THE INVENTION

The characterization of the state of cells and tissues is one of the most demanding issues in medical and biological diagnostics. The problem in performing proper characterization has become increasingly important for the localization of tumorous tissue in the gastrointestinal (GI) tract, discrimination between adenomatous polyps from normal colonic tissue and hyperplastic polyps. The vast majority of colorectal carcinomas arise from adenomatous polyps, wherein the occurance of colorectal carcinomas ranks second only to lung cancer in the United States.

Different types of early detection methods have been suggested over the past decade. For example, an appraisal of pathological conditions of many lesions or abnormalities can be made be endoscopic observation alone, but there remains a margin for error that can be substantial for certain types of lesions. Furthermore, certain abnormalities of a microscopic nature, such as dysplasia, are usually unrecognizable by gross endoscopic observation. Microscopic assessment of biopsy specimens is necessary for many lesions discovered during endoscopy.

The fluorescence properties of fluorophores important in metabolism are characteristic of the states of cells and tissues. Conventional laser fluroscopes are valuable systems to measure sensitive autofluorescence signals of various samples. While this approach causes minimal disturbances to the specimen, conventional systems lack the required spatial resolution and therefore can be used only for local characterization.

Accordingly, there remains no adequate existing in vivo solution to appropriately identify and characterize abnormality conditions. It would therefore be desirable to provide an endoscopic apparatus that was capable of overcoming the difficulties associated with conventional approaches discussed above.

SUMMARY OF THE INVENTION

A hyperspectral imaging endoscopy apparatus is provided that utilizes spectral technology to acquire, process and exploit gastroscopic data. The apparatus allows for real time anomaly detection and identification. The apparatus includes an endoscope, a spectrometer and a processing unit that perform hyperspectral analysis on spectral data generated from the spectrometer. The endoscope and associated coupling optics are preferably optimized for cylindrical symmetry, thus allowing continuous inspection of gastrointestinal or arterial walls.

More specifically, the apparatus includes an endoscope including at least one imaging channel, a spectrometer coupled to the imaging camera, for example, an ICCD, CCD, CMOS or other type of imaging cameras, that generates spectral data in response to an optical signal received from the imaging channel, an optical coupling system that couples an output from the imaging channel to an input of the spectrometer, and a processing unit that performs hyperspectral analysis on the spectral data generated by the spectrometer to generate hyperspectral data. The processing unit correlates the hyperspectral data to spectral characteristics of abnormal tissue to thereby identify abnormal tissue or anomalies imaged by the endoscope through the imaging channel through the use of hyperspectral object detection algorithms.

In a preferred embodiment, a display is coupled to the processor, wherein the hyperspectral data is displayed on the display as a hyperspectral image. In addition, an imaging channel is optional provided that is coupled to an electronic imaging camera. The electronic imaging camera generates conventional image data that can also be viewed on the display as a standard image. If desired, the hyperspectral image and the standard image are simultaneously displayed to allow side-by-side comparison by a physician or operator.

The optical coupling system includes a prism and a mechanism that rotates the prism to rotate the output of the imaging channel with respect to the input of the spectrometer. When the prism is utilized, it is preferable to convert the hyperspectral data prior to display such that the hyperspectral image dimensionally corresponds with the standard image.

Alternatively, the optical coupling system includes a mirror and means for moving the mirror to translate the output of the imaging channel with respect to an input of the spectrometer.

Various features and advantages of the invention will become further apparent to those skilled in the art from the following detailed description of the preferred embodiments of the invention.

BRIEF DESCRIPTION OF THE DRAWINGS

The invention will be described with referenced to certain preferred embodiments thereof with reference to the accompanying drawings, wherein.

DETAILED DESCRIPTION OF THE PREFERRED EMBODIMENTS

Figure 1:
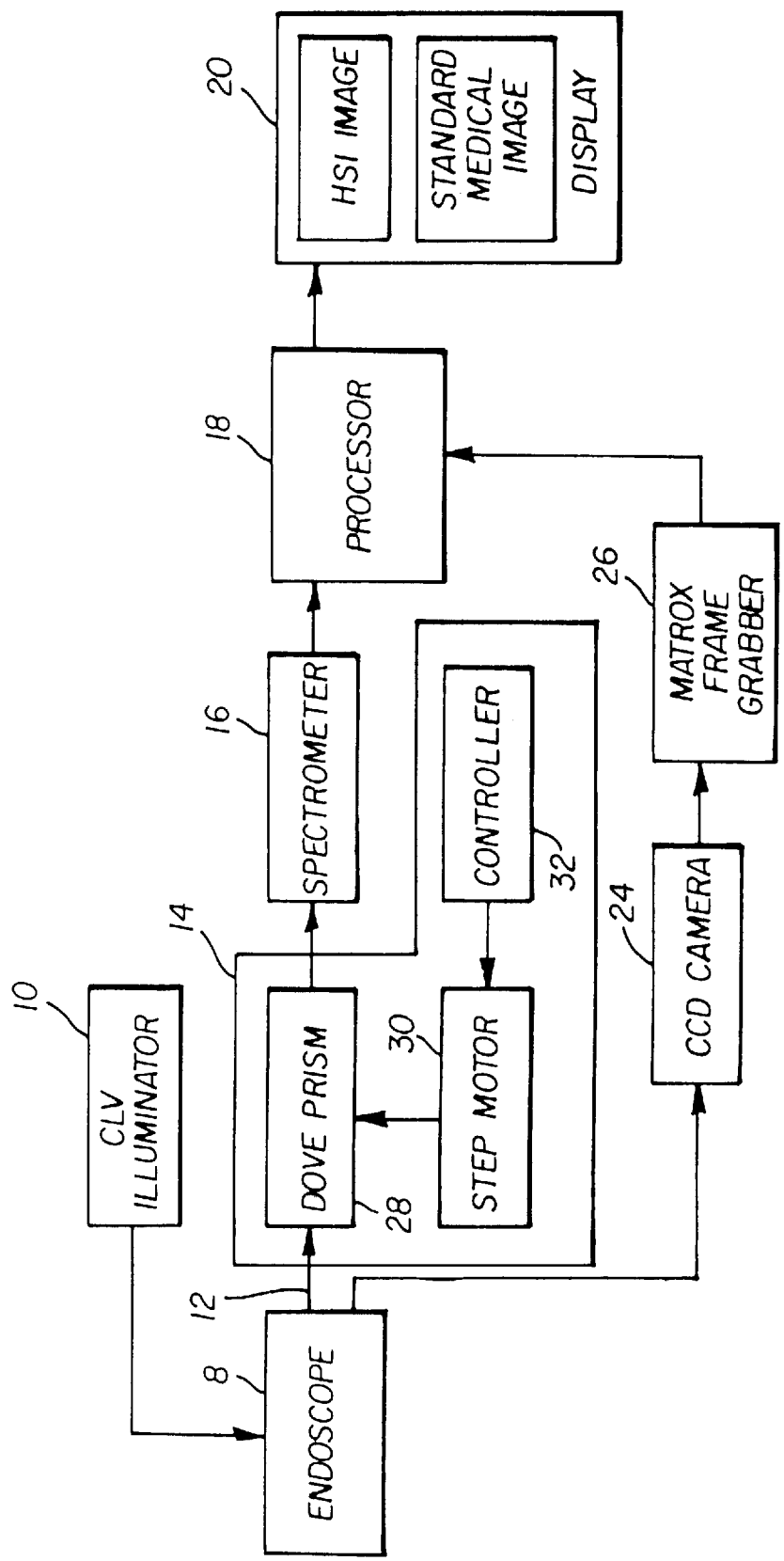
FIG. 1 is a schematic block diagram of an apparatus in accordance with a first embodiment of the invention.

A basic block diagram of a hyperspectral endoscopic apparatus in accordance with the invention is illustrated in FIG. 1. A conventional endoscope 8, for example an Olympus GIF 2T10 scope, is modified to include a hyperspectral imaging channel 12 inserted into the biopsy channel. A fiber optic bundle, for example, is inserted into the biopsy channel to be utilized as the hyperspectral imaging channel 12. Illumination is provided by a conventional illuminator 10, for example, an Olympus CLV-10 illuminator. The hyperspectral imaging channel 12 is coupled to a spectrometer 16 via an optical coupling system 14. A spectral output data from the spectrometer 16, for example an imaging spectrometer made by Americal Holography, Co. coupled to a Pixel Vision CCD camera, is provided to a processing unit 18, which processes the spectral output signal utilizing hyperspectral analysis processing to create a hyperspectral data. The processing unit 18 correlates the hyperspectral data to known spectral characteristics of tissue having abnormalities or anomalies within the GI tract.

In the illustrated embodiment, the hyperspectral data is displayed as a hyperspectral image on a display unit 20. A conventional imaging channel 22 of the endoscopic 10 is coupled to a conventional CCD camera 24 (Olympus CCD Camera OTV S2). The conventional electronic image data from the CCD camera 24 is provided to a matrix frame grabber 26 (Matrox 12 Video Board), which grabs and supplies an image frame to the processor 18 for display on the display unit 20 as a conventional standard image of the GI tract. Accordingly, both the hyperspectral image and the standard medical image can be displayed side-by-side for comparison. The images are preferably stored as avi_files, which can be later transferred and read by video player programs.

The GI symmetry and the location of targets of interest, i.e. tissue abnormalities, on the GI wall are cylindrical in nature. The spectrometer 16, however, utilizes a narrow slit. In order to use all imaging features of hyperspectral analysis of the GI image, it is desirable to rotate the slit with respect to scene being imaged. In a preferred embodiment, this is accomplished by providing the optical coupling system 14 with a Dove prism 28 in the optical path. The Dove prism 28 is rotated by a motor 30 under control of a linear controller 32 (for example a Sherline Products CNC P/N 8800). The Dove prism 28 rotates the image at the twice angle. Thus, full image collection requires only a ninety degree rotation.

The use of the Dove prism 28 creates a visually complicated picture that combines both spatial and spectral features in the displayed hyperspectral image. In essence, the movement of the endoscope 10 through the GI tract, coupled with the rotation of the image through the Dove prism 28, results in a hyperspectral image corresponding to a "corkscrew" type scan through the GI tract. In fact, the appearance of the hyperspectral image is irrelevant with respect to the ability to identify and locate tissue abnormalities, as the processor 18 can correlate detected abnormalities to actual positions within the GI tract based on knowledge of the scan rate. However, for viewing purposes, it is desirable to have the processor 18 convert the hyperspectral data resulting from the use of the Dove prism 28 to a hyperspectral image that dimensionally corresponds to the standard medical image displayed on the display 20. Thus, highlighted abnormalities in the hyperspectral image can be visually correlated more directly to the "real world" standard medical image.

Figure 2:
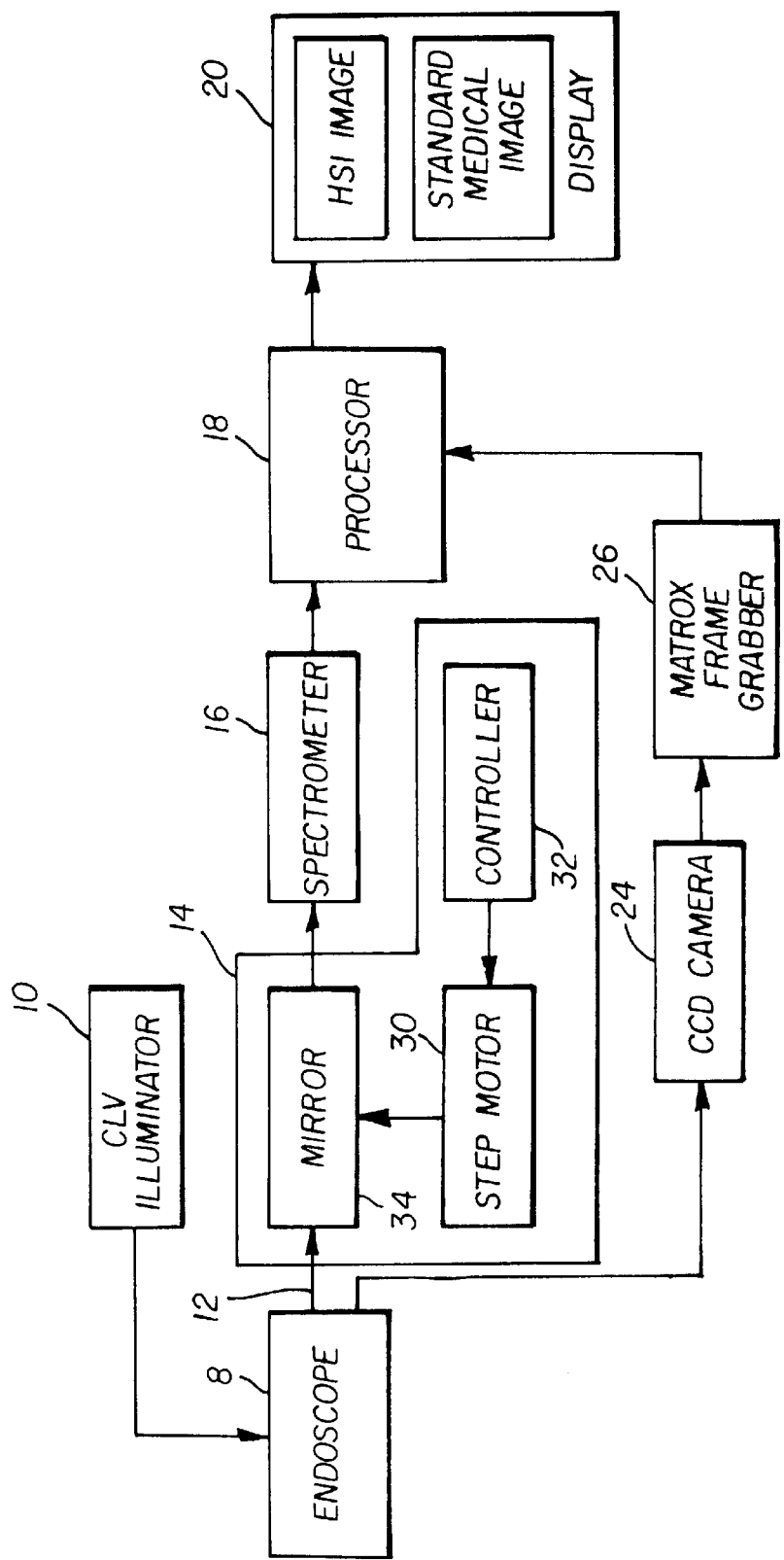
FIG. 2, is a schematic block diagram of an apparatus in accordance with a second embodiment of the invention.

Alternatively, the Dove prism 28 can be replaced by a scanning mirror 34 as illustrated in FIG. 2. In this embodiment, the motor 30 causes the scanning mirror 34 to essentially scan the image across the slit of the spectrometer 16. Accordingly, the hyperspectral data that is generated corresponds to slices or segments that, from the image processing viewpoint, are easier to reconstruct.

It should be understood, however, that the actual display of the hyperspectral data need not be performed. For example, the processor 18 need only perform the hyperspectral analysis on the spectral data received from the spectrometer 16 and correlate the results with known spectral responses of abnormal tissue. Instead of actually displaying an image based on the hyperspectral data, the location and identification of the abnormal tissue can be conveyed to the physician through other means. As one example, markers can be provided on the standard medical image displayed on the display 20, so that the physician can view the location of interest.

The use of spectral data to detect abnormal tissue in itself is known. U.S. Pat. Nos. 5,507,287 and 5,769,792 both entitled "Endoscopic Imaging System for Diseased Tissue", the contents of each of which are incorporated herein by reference, discuss the limited utilization of discrete spectral bands. Hyperspectral analysis, however, utilizes continuous coverage of a given spectral range. Analysis of the hyperspectral data exploits geometric properties of the data in hyperspace as well as spectral features. For example, the use of hyperspectral processing for object identification is described in U.S. Pat. No. 6,038,344 entitled "Intelligent Hypersensor Processing System", the contents of which are incorporated herein by reference, and U.S. Pat. No. 6,167,156 entitled "Compression of Hyperdata with ORASIS Multi-Segment Pattern Sets (CHOMPS)", the contents of which are incorporated herein by reference. As hyperspectral analysis includes both spectral and spatial dimensionality analysis, it can be utilized to not only identify the characteristics of an isolated location point or object, but also to identify that local point or object within an imaged field.

The invention has been described with reference to certain preferred embodiments thereof. If will be understood, however, that modifications and variations are possible within the scope of the appended claims.

What is claimed is:

1. An apparatus comprising:
   an endoscope including at least one imaging channel;
   a spectrometer that generates spectral data in response to an optical signal;
   an optical coupling system that couples an output from the imaging channel to an input of the spectrometer; and
   a processing unit that performs hyperspectral analysis on the spectral data generated by the spectrometer to generate hyperspectral data;
   wherein said optical coupling system includes a mechanism that performs one of rotation and translation of the output of the imaging channel with respect to the input of the spectrometer.

2. An apparatus as claimed in claim 1, wherein the processing unit correlates the hyperspectral data to spectral characteristics of abnormal tissue to thereby identify abnormal tissue imaged by the endoscope through the imaging channel.

3. An apparatus as claimed in claim 1, further comprising a display coupled to the processing unit, wherein the hyperspectral data is displayed on the display as a hyperspectral image.

4. An apparatus as claimed in claim 3, further comprising an imaging channel coupled to an electronic imaging camera that generates electronic image data, wherein the electronic image data is displayed as a standard image on the display.

5. An apparatus as claimed in claim 4, wherein the hyperspectral image and the standard image are simultaneously displayed on the display.

6. An apparatus as claimed in claim 1, wherein the mechanism comprises a prism and means for rotating the prism to rotate the output of the imaging channel with respect to the input of the spectrometer.

7. An apparatus as claimed in claim 1, wherein the mechanism comprises a mirror and means for moving the mirror to translate the output of the imaging channel with respect to an input of the spectrometer.

* * * * *